United States Patent
Davies et al.

(10) Patent No.: US 8,753,319 B2
(45) Date of Patent: Jun. 17, 2014

(54) DRUG DELIVERY SYSTEM

(75) Inventors: James Alexander Davies, Warwickshire (GB); Steven Wimpenny, Warwickshire (GB); Daniel Thomas De Sausmarez Lintell, Warwickshire (GB); David Sanders, Warwick (GB); Paul Richard Draper, Worcestershire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 13/881,805

(22) PCT Filed: Oct. 31, 2011

(86) PCT No.: PCT/EP2011/069098
§ 371 (c)(1),
(2), (4) Date: Apr. 26, 2013

(87) PCT Pub. No.: WO2012/059453
PCT Pub. Date: May 10, 2012

(65) Prior Publication Data
US 2013/0218087 A1 Aug. 22, 2013

Related U.S. Application Data

(60) Provisional application No. 61/432,708, filed on Jan. 14, 2011.

(30) Foreign Application Priority Data

Nov. 3, 2010 (EP) .................................. 10189783

(51) Int. Cl.
*A61M 5/00* (2006.01)
(52) U.S. Cl.
USPC .......................................... 604/191; 604/218

(58) Field of Classification Search
USPC ............. 604/89–90, 91–92, 191, 204, 85–88, 604/218
See application file for complete search history.

(56) References Cited

U.S. PATENT DOCUMENTS 5,637,087 A * 6/1997 O'Neil et al. .................. 604/82
(Continued)

FOREIGN PATENT DOCUMENTS

FR 1320820 3/1963

OTHER PUBLICATIONS

International Search Report and Written Opinion for Int. App. No. PCT/EP2011/069098, mailed Feb. 21, 2012.
Written Opinion for Int. App. No. PCT/EP2011/069098, mailed Jan. 3, 2013.

(Continued)

*Primary Examiner* — Nicholas Lucchesi
*Assistant Examiner* — Melissa A Snyder
(74) *Attorney, Agent, or Firm* — McDonnell Boehnen Hulbert & Berghoff LLP

(57) ABSTRACT

A method and system for delivering a user-settable dose of a first medicament and a non-user settable dose of a second medicament through a single dose setter and a single dispense interface. The drug delivery system includes a drug delivery device and a medicated module. The drug delivery device comprises a single dose setter operably connected to a primary reservoir containing the first medicament. The medicated module comprises (i) a collapsible feature holding the second medicament and (ii) the single dispense interface having an output needle. Further, the drug delivery device and medicated module are each configured such that the single dose setter is mechanically linked to the collapsible feature after attachment of the medicated module to the drug delivery device.

15 Claims, 6 Drawing Sheets

(56) References Cited

U.S. PATENT DOCUMENTS 6,562,002 B1 5/2003 Taylor
2006/0229562 A1 10/2006 Marsh et al.
2006/0276755 A1 12/2006 Sullivan

OTHER PUBLICATIONS

International Preliminary Report on Patentability for Int. App. No. PCT/EP2011/069098, mailed Feb. 28, 2013.

\* cited by examiner

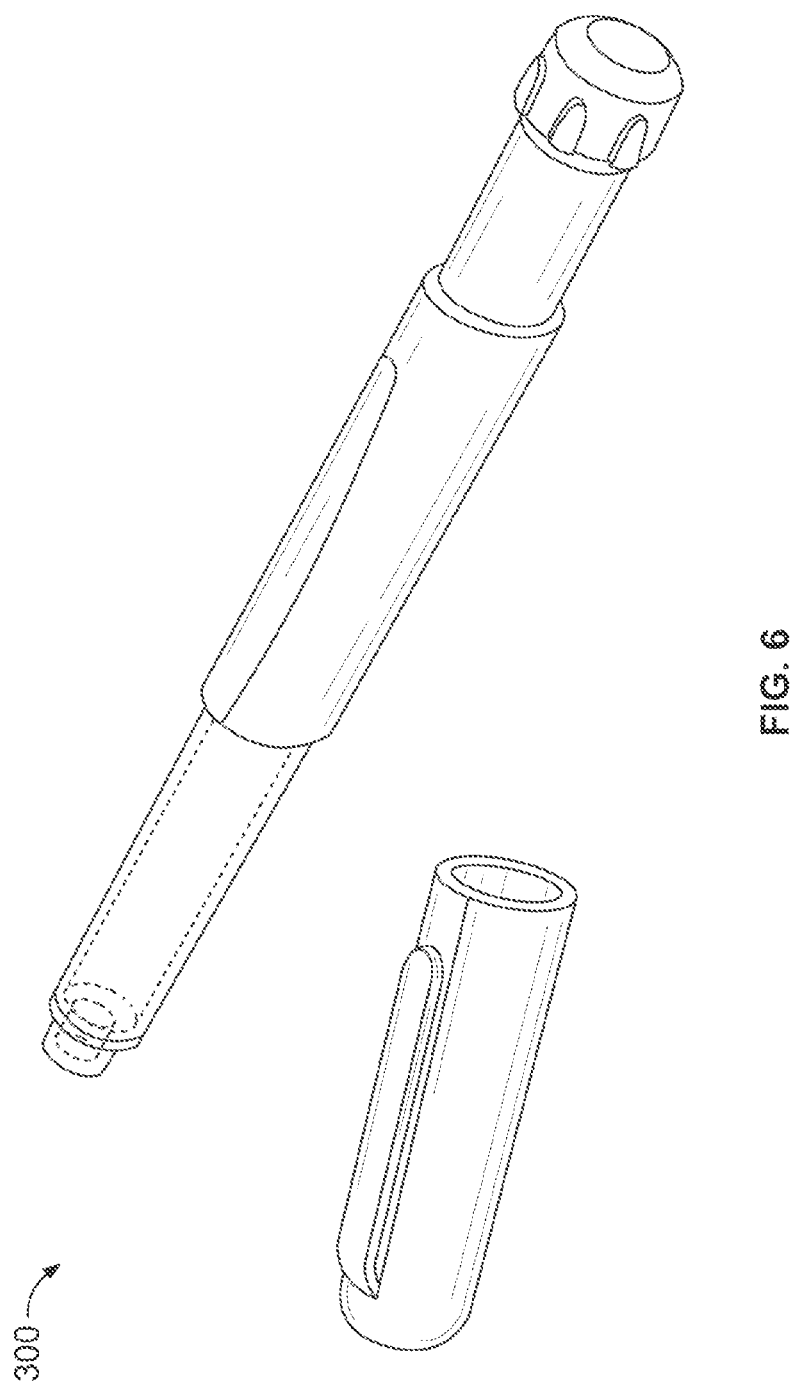

DRUG DELIVERY SYSTEM

CROSS REFERENCE TO RELATED APPLICATIONS

The present application is a U.S. National Phase Application pursuant to 35 U.S.C. §371 of International Application No. PCT/EP2011/069098 filed Oct. 31, 2011, which claims priority to European Patent Application No. 10189783.3 filed Nov. 3, 2010 and U.S. Provisional Patent Application No. 61/432,708 filed Jan. 14, 2011. The entire disclosure contents of these applications are herewith incorporated by reference into the present application.

FIELD OF THE DISCLOSURE

This present patent application relates to medical devices and methods of delivering at least two drug agents from separate reservoirs using drug delivery systems having only a single dose setting mechanism and a single dispense interface. A single delivery procedure initiated by the user causes a non-user settable dose of a second drug agent and a variable set dose of a first drug agent to be delivered to the patient. The drug agents may be available in two or more reservoirs, containers or packages, each containing independent (single drug compound) or pre-mixed (co-formulated multiple drug compounds) drug agents. Specifically, this application concerns a drug delivery system having a collapsible feature holding a secondary medicament, where the collapsible feature is compressed during the drug dispense process.

BACKGROUND

Certain disease states require treatment using one or more different medicaments. Some drug compounds need to be delivered in a specific relationship with each other in order to deliver the optimum therapeutic dose. The presently proposed devices and methods are of particular benefit where combination therapy is desirable, but not possible in a single formulation for reasons such as, but not limited to, stability, compromised therapeutic performance and toxicology.

For example, in some cases it might be beneficial to treat a diabetic with a long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems that can arise when delivering two active medicaments or "agents" simultaneously. The two active agents may interact with each other during the long-term, shelf life storage of the formulation. Therefore, it is advantageous to store the active components separately and combine them at the point of delivery, e.g. injection, needle-less injection, pumps, or inhalation. However, the process for combining the two agents needs to be simple and convenient for the user to perform reliably, repeatedly and safely.

A further problem is that the quantities and/or proportions of each active agent making up the combination therapy may need to be varied for each user or at different stages of their therapy. For example, one or more active agents may require a titration period to gradually introduce a patient up to a "maintenance" dose. A further example would be if one active agent requires a non-adjustable fixed dose while the other is varied in response to a patient's symptoms or physical condition. This potential problem means that pre-mixed formulations of multiple active agents may not be suitable as these pre-mixed formulations would have a fixed ratio of the active components, which could not be varied by the healthcare professional or user.

Additional problems arise where a multi-drug compound therapy is required, because many users cannot cope with having to use more than one drug delivery system or make the necessary accurate calculation of the required dose combination. This is especially true for users with dexterity or computational difficulties. Additional issues may arise due to the ullage volume left in a drug delivery device post dispense. For instance, a large ullage volume may result in a large volume of "un-used or "wasted medicament.

SUMMARY

Accordingly, there exists a need to provide devices and methods for the delivery of two or more medicaments in a single injection or delivery step that is straight forward for the user to perform and that limits or minimizes the ullage volume left in the drug delivery device post dispense. The presently proposed devices and methods overcome the above-mentioned problems by providing separate storage containers for two or more active drug agents. Specifically, the presently proposed devices and methods provide a collapsible feature or container that holds the second medicament. A user sets a dose of one medicament (i.e., a user settable dose). The dose of the second medicament is independently controlled and therefore is not influenced by an amount of the user settable dose. (i.e., non-user settable). The drug agents are then delivered to the patient during a single delivery procedure. Beneficially, the collapsible feature or container holding the second medicament is compressed during drug delivery, and this compression serves to reduce or minimize the ullage volume left post dispense in the medicated module comprising the collapsible container.

The proposed devices and methods also give the opportunity for varying the quantity of one or both medicaments. For example, one fluid quantity can be varied by changing the properties of the injection device (e.g., dialing a user variable dose or changing the device's "fixed" dose). The second fluid quantity can be changed by manufacturing a variety of secondary drug containing packages with each variant containing a different volume and/or concentration of the second active agent. The user or healthcare professional would then select the most appropriate secondary package or series or combination of series of different packages for a particular treatment regime. The proposed medicated module comprises a self-contained reservoir in which a non-user-settable dose of a medicament may be stored.

These and other advantages will become evident from the following more detailed description of the invention.

The presently proposed systems and methods allow for complex combinations of multiple drug compounds within a single drug delivery system. The proposed systems and methods allow the user to dispense at least two drug agents through one single dose setting mechanism and a single dispense interface. This single dose setter controls the dosing mechanism of the system such that a predefined combination of the individual drug compounds is delivered when a single dose of one of the medicaments is set and dispensed through the single dispense interface. Further, the presently proposed systems and methods minimize ullage left in the medicament container within the medicated module of the drug delivery system post dispense.

By defining the therapeutic relationship between the individual drug compounds, the proposed drug delivery systems and delivery methods help ensure that a patient/user receives the optimum therapeutic combination dose from a multi-drug compound device without the inherent risks associated with multiple inputs where the user has to calculate and set the correct dose combination every time they use the system. The medicaments can be fluids, defined herein as liquids or gases or powders that are capable of flowing and that change shape at a steady rate when acted upon by a force tending to change its shape. Alternatively, one or both of the medicaments may be a solid that is carried, solubilized or otherwise dispensed with another fluid medicament.

Applicants' proposed concept is of particular benefit to users with dexterity or computational difficulties as the single input and associated predefined therapeutic profile removes the need for them to calculate their prescribed dose every time they use the system and the single input allows considerably easier setting and dispensing of the combined compounds.

In a preferred embodiment a master drug compound, such as insulin, contained within a multiple dose, user selectable drug delivery device could be used with a single use, user replaceable, medicated module that contains a single dose of a secondary medicament and the single dispense interface. When connected to the primary drug delivery device, the secondary compound is activated/delivered on dispense of the primary compound. Although the present application specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with our proposed methods and systems.

For the purposes of our proposed methods and systems the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg (B32) human insulin; Lys(B3), Glu(B29) human insulin; Lys (B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B-29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2), Exendin-3, Liraglutide, or AVE0010 (H-His-Gly-Glu-Gly-Thr-Phe-Thr-Ser-Asp-Leu-Ser-Lys-Gln-Met-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH2).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

According to an example, a drug delivery system to deliver a user-settable dose of a first medicament and a non-user settable dose of a second medicament through a single dose setter and a single dispense interface is provided. The drug delivery system comprises a drug delivery device and a medicated module attachable to the drug delivery device. The drug delivery device comprises an outer housing disposed around a single dose setter operably connected to a primary reservoir of medicament including the first medicament. The drug delivery device further comprises a dose button operably connected to the primary reservoir of medicament, a push rod axially moveable with respect to the outer housing, and a biasing feature operably connected to the push rod.

The medicated module comprises a first needle, a second needle, and a collapsible feature or container holding the second medicament, wherein the first needle and second needle are in fluid communication with the collapsible feature and the medicated module is configured to be attached to a drug delivery device. After the medicated module is attached to the drug delivery device, the first needle is in fluid communication with the primary drug reservoir. Further, during dispense, (i) axial displacement of the dose button forces the first medicament to flow from the reservoir into the collapsible feature via the first needle, (ii) axial displacement of the dose button forces medicament in the collapsible feature to flow out of the second needle and (iii) at a predetermined axial displacement of the dose button, the dose button forces the push rod to overcome a preloaded force of the biasing feature and move axially in the distal direction. The axial movement of the push rod compresses the collapsible feature, and the compression of the collapsible feature forces at least some of a remaining amount of medicament in the collapsible feature out of the second needle. Other drug delivery systems comprising a collapsible feature are possible as well.

According to another example, the medicated module comprises a collapsible feature positioned between a first needle and a second needle.

According to another embodiment, a method of dispensing a user settable dose of a first medicament and a non-user-settable dose of a second medicament using a single dispense interface is provided. The method includes the step of attaching a medicated module to a drug delivery device. The drug delivery device comprises a single dose setter operably connected to a primary reservoir containing the first medicament. Further, the medicated module comprises (i) a collapsible feature holding the second medicament and (ii) the single dispense interface having an output needle. The drug delivery device and medicated module are each configured such that the single dose setter is mechanically linked to the collapsible feature after attachment of the medicated module to the drug delivery device. The method further includes the step of setting a dose of the first medicament contained in the primary drug reservoir using the single dose setter of the drug delivery device. Still further, the method includes the step of activating a dose button of the single dose setter to cause the dose of the first medicament from the primary drug reservoir to the collapsible feature. And yet still further, the method includes the steps of forcing medicament in the collapsible feature to flow out the output needle and forcing the mechanically-linked dose setter to compress the collapsible feature, thereby forcing at least some of a remaining amount of medicament in the collapsible feature out the output needle.

A medicated module in accordance with Applicants' proposed concept can be designed for use with any system with an appropriate compatible interface. However, it may be preferable to design the module in such a way as to limit its use to one exclusive primary drug delivery device (or family of devices) through employment of dedicated or coded features to prevent attachment of a non-appropriate medicated module to a non-matching device. In some situations it may be beneficial to ensure that the medicated module is exclusive to one drug delivery device while also permitting the attachment of a standard drug dispense interface to the device. This would allow the user to deliver a combined therapy when the module is attached, but would also allow delivery of the primary compound independently through a standard drug dispense interface in situations, such as, but not limited to, dose splitting or top-up of the primary compound.

A particular benefit of Applicants' methods and systems is that the methods and systems serve to limit or minimize the amount of ullage left in the medicated module post use (relative to the volume of the fixed dose of medicament in the module prior to use). Thus, Applicants' proposed methods and systems serve to limit the amount of medicament that may be wasted by being left in the medicated module post dispense.

In a preferred embodiment, the primary drug delivery device is used more than once and therefore is a multi-use device; however, the drug delivery device may also be a single use disposable device. Such a device may or may not have a replaceable reservoir of the primary drug compound, but Applicants' proposed concept is equally applicable to both scenarios. It is also possible to have a suite of different medicated modules for various conditions that could be prescribed as one-off extra medication to patients already using a standard drug delivery device. Should the patient attempt to reuse a previously used medicated module, features may be present that prevent reattachment to a primary drug delivery device or that prevent or discourage subsequent dosing through the needle via alternative means. For example, this module may include a locking needle guard that is activated after a user delivers a dose from the medicated module. Other means of alerting the user may include some (or all) of the following:

Physical prevention of medicated module re-attachment to the primary drug delivery device once the module has been used and removed.

Physical/hydraulic prevention of subsequent liquid flow through the drug dispense interface once it has been used.

Physical locking of the dose setter and/or dose button of the primary drug delivery device.

Visual warnings (e.g., change in color and/or warning text/indicia within an indication window on the module once insertion and/or fluid flow has occurred).

Tactile feedback (presence or absence of tactile features on the outer surface of the module hub following use).

A further proposed feature is that both medicaments are delivered via one injection needle and in one injection step. This offers a convenient benefit to the user in terms of reduced user steps compared to administering two separate injections. This convenience benefit may also result in improved compliance with the prescribed therapy, particularly for users who find injections unpleasant or who have computational or dexterity difficulties.

A further independent aspect of the invention relates to a medicated module attachable to a drug delivery device, the drug delivery device comprising a housing, a reservoir for a liquid, and a dose button. The medicated module comprises a first needle, a second needle, and a collapsible feature for holding a medicament, wherein the first needle and second needle are in fluid communication with the collapsible feature. The medicated module further comprises a biasing feature preloaded with a force, wherein, after the medicated module is attached to the drug delivery device, (i) the first needle is in fluid communication with the reservoir of the drug delivery device and (ii) the biasing feature is configured to prevent compression of the collapsible feature until a predetermined displacement of the dose button. During dispense, the preload of the biasing feature can be overcome at the predetermined displacement of the dose button (12) to allow compression of the collapsible feature. Furthermore, during dispense (i) the first medicament may flow from the reservoir into the collapsible feature via the first needle, (ii) displacement of the dose button may force medicament in the collapsible feature to flow out of the second needle and (iii) at the predetermined displacement of the dose button, the preloaded force of the biasing feature is overcome to allow compression of the collapsible feature, wherein compression of the collapsible feature forces at least some of a remaining amount of medicament in the collapsible feature out of the second needle.

Alternatively, a medicated module is attachable to a drug delivery device, the drug delivery device comprising a housing, a reservoir for a liquid, and a dose button. The medicated module comprises a first needle, a second needle, and a collapsible feature for holding a medicament, wherein the first needle and second needle are in fluid communication with the collapsible feature. The first needle may be configured to establish fluid communication with the liquid in the drug delivery device's reservoir, the second needle may be configured for dispensing liquid, and the collapsible feature may be arranged between and in fluid communication with the first needle and second needle. After the medicated module is attached to the drug delivery device, the first needle is in fluid communication with the reservoir of the drug delivery device. During dispense the compression of the collapsible feature is allowed.

A biasing feature is configured to prevent compression of the collapsible feature until a predetermined displacement of the dose button. The biasing feature may be part of either one of the medicated module and the drug delivery device. The biasing feature may be preloaded with a force. During dispense, the preload of the biasing feature can be overcome at the predetermined displacement of the dose button to allow compression of the collapsible feature.

Furthermore, during dispense (i) the first medicament may flow from the reservoir into the collapsible feature via the first needle, (ii) displacement of the dose button may force medicament in the collapsible feature to flow out of the second needle and (iii) at the predetermined displacement of the dose button, the preloaded force of the biasing feature may be overcome to allow compression of the collapsible feature, wherein compression of the collapsible feature forces at least some of a remaining amount of medicament in the collapsible feature out of the second needle.

A further independent aspect of the invention disclosed herein relates to a drug delivery system to deliver a user-settable dose of a first medicament and a non-user settable dose of a second medicament through a single dose setter and a single dispense interface. The drug delivery system comprising a drug delivery device comprising an outer housing disposed around a single dose setter operably connected to a primary reservoir of medicament including the first medicament, a dose button operably connected to the primary reservoir of medicament, and a push rod axially moveable with respect to the outer housing. The drug delivery system further comprises a medicated module as disclosed herein attachable to the drug delivery device wherein the biasing feature of the medicated module is operably connected to the push rod of the drug delivery device when the medicated module is attached to the drug delivery device. During dispense at a predetermined displacement of the dose button, the dose button forces the push rod to move axially in the distal direction, wherein the axial movement of the push rod compresses the collapsible feature, and wherein the compression of the collapsible feature forces at least some of the remaining amount of the medicament in the collapsible feature out of the second needle.

A further independent aspect of the invention relates to another drug delivery system to deliver a user-settable dose of a first medicament and a non-user settable dose of a second medicament through a single dose setter and a single dispense interface comprising a drug delivery device and a medicated module. The drug delivery device of such system comprising a housing including the single dose setter operably connected to a primary reservoir of medicament including the first medicament, a dose button operably connected to the primary reservoir of medicament, and an outer shroud. The outer shroud holds the drug delivery device and the drug delivery device is axially moveable relative to the outer shroud. The medicated module of such drug delivery system is according to the disclosure of this invention comprising a biasing feature preloaded with a force and is attachable to the drug delivery device. The biasing feature is operably connected to a distal internal surface of the outer shroud and a distal external surface of the drug delivery device when in attached condition. During dispense, (i) axial displacement of the dose button may force the first medicament to flow from the primary reservoir into the collapsible feature via the first needle, (ii) axial displacement of the dose button may force medicament in the collapsible feature to flow out of the second needle and (iii) at a predetermined axial displacement of the dose button, the drug delivery device overcomes a preloaded force of the biasing feature and moves axially through the outer shroud, wherein the axial movement of the drug delivery device compresses the collapsible feature. The compression of the collapsible feature may forces at least some of a remaining amount of medicament in the collapsible feature out of the second needle. Furthermore during dispense, at a predetermined displacement of the dose button, the drug delivery device may overcome the preloaded force of the biasing feature and move axially through the outer shroud, wherein the axial movement of the drug delivery device may compress the collapsible feature, wherein the compression of the collapsible feature may force at least some of the remaining amount in the collapsible feature out of the second needle.

A further independent aspect of the invention relates to a drug delivery system to deliver a user-settable dose of a first medicament and a non-user settable dose of a second medicament through a single dose setter and a single dispense interface comprising a drug delivery device and a medicated module. The medicated module comprises a collapsible feature for holding a medicament. The system further comprises a biasing feature configured to prevent compression of the collapsible feature. When the medicated module is attached to the drug delivery device, the biasing feature may prevent compression of the collapsible feature until a predetermined displacement of a dose button of the drug delivery device. The biasing feature may be preloaded with a force. The biasing feature may be part of the drug delivery device, the medicated module, or an additional component, e.g. an outer shroud that is attached to the drug delivery device.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIG. 6 illustrates an example drug delivery device.

DETAILED DESCRIPTION

Applicants' proposed concept is a system and method for dispensing a non-user settable dose of one medicament and a user-settable dose of a primary medicament using a single dispense interface. Beneficially, Applicants' proposed concept serves to minimize or limit the ullage volume left in a medicated module of the proposed drug delivery system (relative to an original volume of a secondary medicament in the medicated module of Applicants' system (prior to use)).

Figure 1A:
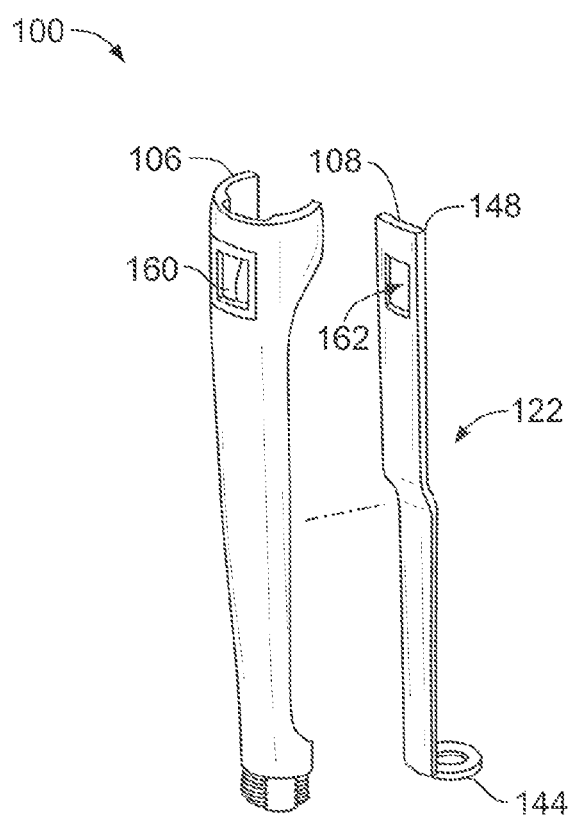
FIGS. 1A-C illustrate a perspective views of an exemplary drug delivery system.
Figure 1B:
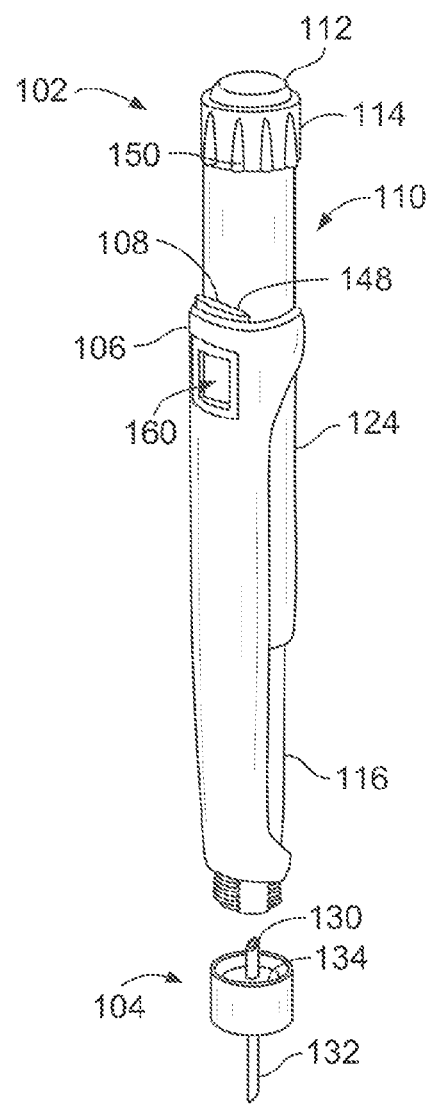
Figure 1C:
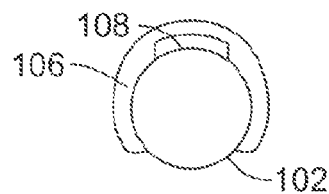

FIGS. 1A-C illustrate an example drug delivery system 100 in accordance with an embodiment of Applicants' proposed concepts. The drug delivery system 100 is operable to deliver a user-settable dose of a first medicament and a non-user settable dose of a second medicament through a single dose setter and a single dispense interface. Generally, drug delivery system 100 includes a drug delivery device 102 and a medicated module 104.

The drug delivery device 102 comprises an outer housing 106, a push rod 108, and a single dose setter 110. The push rod 108 is generally encased by the outer housing 106. For clarity, FIG. 1A illustrates a partially exploded view of the drug delivery system 100, since the majority of the push rod 108 is concealed in the non-exploded view. As will be described in greater detail below, the push rod 108 serves to mechanically link the dispensing mechanism (i.e., dose setter 110) to the collapsible feature in the medicated module 104.

Figure 2:
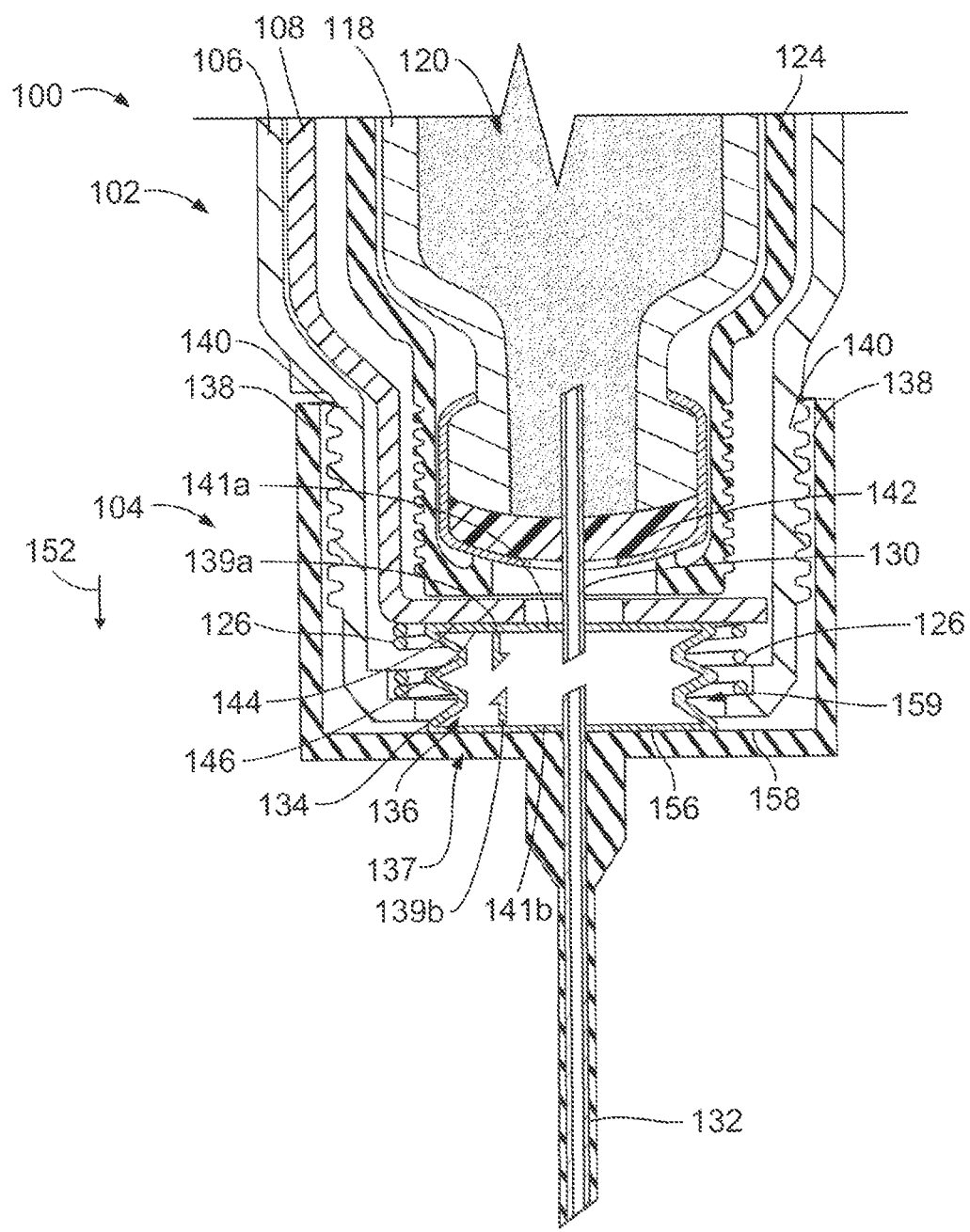
FIG. 2 illustrates a cross-sectional view of an exemplary medicated module attached to an exemplary drug delivery device.

The dose setter 110 includes a dose button 112 and a dose dial 114. The dose setter 110 may be operably connected to a primary reservoir of medicament that may be stored in the drug delivery system 100, such as in cartridge holder 116. Cartridge holder 116 may hold primary reservoir 118 of the first medicament 120, as shown in FIG. 2. In this example depicted in FIGS. 1A-C, the single dose setter 110 is housed by an inner housing 124. This inner housing may be the outer housing of a standard drug delivery device, such as the standard drug delivery device 300 shown in FIG. 6. In accordance with this example, the outer housing 106 and the push rod 108 may be assembled over a typical drug delivery device. This assembly may be performed at various stages. For example, this assembly may be performed during the manufacturing process. Alternatively, this assembly may be performed by a trained medical personnel or, for that matter, a user of the drug delivery system. However, it should be understood that the drug delivery system 100 need not include a standard drug delivery device housed by outer housing 106. Rather, the system 100 could be manufactured as a single stand-alone unit.

Likewise, the medicated module (104, 204) can be a stand-alone device comprising a first needle (130, 230), a second needle (132, 232), a collapsible feature (134, 234, 534) holding a medicament (136, 236, 536), wherein the first needle (130, 230) and second needle (132, 232) are in fluid communication with the collapsible feature (134, 234, 534). After the medicated module (104, 204) is attached to the drug delivery device (102, 202, 502), (i) the first needle (130, 230) is in fluid communication with the reservoir (118, 218, 518) of the drug delivery device and (ii) the biasing feature (126, 226, 526) biases the drug delivery device (102, 202, 502) to prevents the drug delivery device (102, 202, 502) from substantially compressing of the collapsible feature (134, 234, 534). During dispense, (i) axial displacement of the dose button (112, 212) forces the first medicament (120, 220, 520) to flow from the primary reservoir (118, 218, 518) into the collapsible feature (134, 234, 534) via the first needle (130, 230), (ii) axial displacement of the dose button (112, 212) forces medicament in the collapsible feature (134, 234, 534) to flow out of the second needle (132, 232) and (iii) at a predetermined axial displacement of the dose button (112, 212), the drug delivery device (102, 202, 502) overcomes a preloaded force of the biasing feature (126, 226, 526) is overcome and moves axially through the outer shroud (206), wherein the axial movement of the drug delivery device (102, 202, 502) to allow compression of the collapsible feature (134, 234, 534), wherein the compression of the collapsible feature (134, 234, 534) forces at least some of a remaining amount of medicament in the collapsible feature (134, 234, 534) out of the second needle (132, 232).

When drug delivery system 100 is assembled, the push rod 108 is axially moveable with respect to the outer housing 106. The body 122 of the push rod is preferably configured to generally conform to the body of the outer housing 106 and/or the body of the inner housing 124.

The system 100 further comprises a biasing feature that is operably connected to the push rod. For example, as seen in FIG. 2, system 100 may include a spring 126 that is operably connected to the push rod 108. It should be understood, however, that other types of biasing features are possible as well. The biasing feature 126 serves to bias the push rod 108 in the axial direction. The operation of the biasing feature 126 during attachment and drug dispense will be described in greater detail below.

As seen in FIG. 1B, medicated module 104 may be attached to the drug delivery device 102. Generally, the medicated module 104 includes a first needle 130, a second needle 132, a collapsible feature 134 holding a second medicament 136. In an example, the second medicament 136 located in the collapsible feature 134 comprises GLP-1 and the first medicament 120 located in the primary drug delivery device 102 comprises insulin. However, other examples of medicaments and combinations of medicaments are possible as well.

The first needle 130 may be referred to herein as an "engagement needle", as the needle engages with or communicates with the reservoir of drug delivery device 102 when the module 104 and device are attached. Further, the second needle 132 may be referred to herein as an "output needle", as the second needle may be used to subcutaneously inject medicament into an injection site, such as an injection site of a user of drug delivery system 100. Further, in an embodiment of Applicants' proposed concept, the medicated module may include a single, double-ended needle that includes an engagement needle portion and an output needle portion in fluid communication with each other. That is, the single, double-ended needle may comprise both the first and second needles discussed above with respect to FIGS. 1-2. In this example, the double-ended needle may have at least one side hole that allows the needle to be in fluid communication with the collapsible feature 134.

The medicated module 104 is depicted in greater detail in FIG. 2. As seen in FIG. 2, the first needle 130 and the second needle 132 are in fluid communication with the collapsible feature 134. Consequently, the first and second needles 130, 132 are in fluid communication with one another. Additionally, the first and second needles 130, 132 are preferably fixed in the medicated module 104. For instance, the needles 130, 132 may be fixed in respective needle hubs 141*a*, 141*b*. These hubs 141*a-b* form the upper and lower surfaces of the collapsible feature 134. As the collapsible feature 134 collapses in one direction (axially), the top and bottom surfaces 141*a-b* may be rigid such that the needles 130, 132 could be fixed in them. The needles 130, 132 could be fixed by gluing, overmoulding, welding (sonically or friction) or other similar processes. In addition, the collapsible feature 134 may be made of several components such that the concertina section which collapses is a non-rigid form therefore permitting an axial reduction in volume during compression. One advantage of such a design is that it would permit the two ends to be rigid elements capable of securing and locating the two needles accurately.

The medicated module 104 also includes an attachment means 138. The attachment means 138 is configured to attach to a corresponding attachment means of a drug delivery device, such as the attachment means 140 of drug delivery device 102.

Further, in an embodiment, the medicated module 104 also includes a needle cover or needle guard (not shown). A needle cover may have a connection feature (e.g., a snap-fit feature) that allows the cover to be removably attached to the body of the medicated module 104. A needle cover or needle guard may substantially conceal the second needle 132 from view so as to reduce needle anxiety that a patient may experience. While concealing the needle, the needle cover or needle guard may also help to prevent inadvertent needle sticks. The needle guard may also be such that once the second needle 132 of the medicated module has been injected into the skin and removed, the guard locks in a position that covers the second needle. This safe position prevents inadvertent needle sticks, but also beneficially prevents a user accidently or consciously using the device for a second time. This prevents the user from using the device a second time thinking that they are receiving the fixed dose of the second medicament 136 when actually they are not. It also prevents a non-sterile needle being used for further injections.

FIG. 2 depicts the medicated module 104 after the module 104 is attached to drug delivery device 102 and prior to the dispense process. Attachment of medicated module 104 to drug delivery device 102 causes the engagement needle 130 to penetrate the septum 142 of the drug cartridge or reservoir 118 of the drug delivery device 102. Once the engagement needle 132 has passed through the septum 142 of the cartridge 118, fluid connection is made between the first medicament 120 and the collapsible feature 134 containing second medicament 136.

As mentioned above, the push rod 108 may be encased within the drug delivery system 100 as shown in FIGS. 1-2. The spring 126 of the drug delivery device 102 is present between the outer housing 106 and the end 144 of the push rod 108. The spring 126 biases the push rod 108 vertically such that contact is made with the end of inner housing 124 that houses cartridge 118.

Upon attachment of the module 104 to device 102, the lower surface (i.e., distal end) 144 of the push rod contacts the top surface 146 of the collapsible feature 134. The distal end 144 of the push rod is disposed between a distal end of the reservoir 118 and a proximal end of the collapsible feature.

The opposite end 148 of the push rod 108 protrudes above the end-stop of the dose dial adjuster, as illustrated in FIG. 1. The push rod 108 preferably protrudes above the end-stop of the dose dial 114 in an amount that is equivalent to how much the collapsible feature will be compressed during drug dispense, which is explained in greater detail below. However, in various alternative examples, the dose dial 114 may protrude above the end-stop more or less than the desired amount of compression.

After the module 104 is attached to the device 102, a user may set a user-settable dose of the first medicament 120. The dose of the drug delivery device may be set in a usual manner (e.g., by dialing out an appropriate number of units of the primary medicament 120 with dose dial 114). In an embodiment, the outer housing and push rod each include respective windows 160, 162, so that a user can see a displayed indication of the units of the dialed dose (e.g., 20-80 units).

Dispense of the first medicament 120 and the second medicament 136 may then be achieved via activation of the dosing mechanism 110 of the drug delivery device 102. Generally, during dispense, axial displacement of the dose button 112 forces the first medicament 120 to flow from the reservoir 118 into the collapsible feature 134 via the first needle 130. Further, axial displacement of the dose button 112 forces medicament in the collapsible feature 134 to flow out of the output needle 132. This medicament in the collapsible feature 134 may be a mixture of first medicament 120 and second medicament 136. Still further, at a predetermined axial displacement of the dose button 112, the dose button forces the push rod 108 to (i) overcome a preloaded force of the biasing feature 126 and (ii) move axially in the distal direction 152. The axial movement of the push rod 108 compresses the collapsible feature 134. This compression of the collapsible feature 134 forces at least some of a remaining amount of medicament in the collapsible feature out of the second needle 132. The remaining amount of medicament may comprise at least one of the first medicament 120 and the second medicament 136, and this will depend on what medicament remains in the collapsible feature 134 at the time of compression.

Specifically, during dispense, depression of the dispensing mechanism 110 of drug delivery device 102 causes the first medicament 120 to (i) flow from the cartridge 118 into the collapsible feature 134 and (ii) thereafter be dispensed through the output needle 132. At a predetermined axial displacement during a dispense stroke, which is preferably substantially near the end of the dispense stroke, the lower surface 150 of the dose dial 114 contacts the top surface 148 of the push rod, causing the push rod 108 to move axially downwards along with the dose dial 114 and dose button 112. As the push rod is displaced axially downwards in direction 152, the lower surface 144 of the push rod compresses the collapsible feature 134. The lower face 156 of collapsible feature 134 may be restrained by the casework 158 of the medicated module. Thus, any force supplied by the push rod 108 will compress the collapsible feature 134, since the collapsible 134 feature is constrained by the distal internal surface 158.

The distal end 144 of the push rod is preferably a shape that is capable of supplying a substantially even amount of force against the proximal surface of the collapsible feature. For instance, as depicted in FIGS. 1 and 2, the distal end 144 may be a circular-ring shape. However, other shapes are possible as well, and the distal end need not be designed to substantially evenly compress the collapsible feature. Further, collapsible feature 134 is preferably configured to compress axially, while generally retaining the same radial extent. The zigzag edges 159 of the collapsible feature 134 allow such axial compression.

Compression of the collapsible feature 134 causes the remaining amount of medicament within the collapsible feature to be dispensed through the output needle 132 and the spring 126 to compress in direction 152. As a practical matter, during dispense, the first medicament 120 and the second medicament 136 can mix with one another during dispense. Thus, the remaining amount of medicament may likely be a mixture of the first and second medicaments. However, it should be understood that in some examples, it may be possible that the medicaments are delivered substantially sequentially (i.e., the second medicament is delivered before the first medicament with limited or no mixing). Therefore, in such an example, the remaining amount of medicament may include only the first medicament.

When the dose dial 114 and dose button 112 is fully depressed, the internal volume of the collapsible feature is reduced, hence minimizing the ullage of the remaining medicament present in the medicated module 104. For example, the internal volume of the compressed collapsible feature may be zero milliliters (ml) or substantially close to zero ml. However, it should be understood that the post-dispense internal volume may be any volume that is less than the pre-dispense internal volume. Other examples of post-dispense internal volume include ¼ or ½ of the pre-dispense internal volume.

After the user finishes dispensing the first medicament 120, the user may remove the output needle 132 from the injection site. Then, the depleted medicated module 104 may be disposed of. Assuming that the drug delivery device 102 still holds some first medicament 120, the drug delivery device 102 may be reused by the patient as required. For instance, a new medicated module may be attached to the drug delivery device.

In an embodiment of Applicants' proposed concept, the system 100 is configured to allow the push rod 108 to return to a pre-dispense position after the push rod 108 compresses the collapsible feature 134. For instance, just prior to full depression of the dose button 112, a recess may be provided in the dose dial 114 of the drug delivery device 102. This allows the push rod 108 to return to the pre-dispense position under the action of the spring 126. In this exemplary arrangement, it is the rotational position of the dose dial sleeve 114 of the drug delivery device 102 relative to the push rod 108 that permits the dose dial sleeve to press on the push rod. As just one example, if the dose dial engages with the pushrod from the 20 unit mark to the 5 unit dose dispense mark, this 'window' would be the time in which the full axial compression of the collapsible feature would be achieved. Once past the 5 unit mark, the push rod 108 could drop into a recess on the underside of the dose dial. This would allow the push rod 108 to return to its starting axial position before attachment of a subsequent module. On dialing the next dose, the dose dial 114 would go past the push rod when setting a dose, but pick it up again during dispense. As such, the push rod is returned to an axial point where the push rod 108 was before the medicated module 104 was attached to the drug delivery device 102 and/or before the dispense process began. Therefore, one advantage of this feature is that it resets the push rod 108 and allows a new medicated module to be attached to the drug delivery device 102 without causing compression of a collapsible feature of the next medicated module.

As mentioned above, in various examples, the dose dial may protrude above the end-stop more or less than the desired amount of compression of the collapsible feature 134. For instance, when attached, the push rod may not yet be in contact with the collapsible feature (e.g., Y millimeters (mm) away). Therefore, in order to collapse the collapsible feature X mm, the push rod may protrude X+Y mm. Accordingly, when the push rod is displaced X+Y mm, the push rod would compress the collapsible feature X mm. In yet another example, the push rod may not protrude at all. As an example, the dose dial 114 may include a protrusion that acts to move the push rod axially before the dose dial reaches the end stop. The end stop may further include a recess that receives the protrusion.

In certain examples of Applicants' proposed concepts, the medicated module may include features that would retain the collapsible feature 134 in its collapsed state following use. For example, as illustrated in FIG. 2 the collapsible feature 134 may further comprise a retaining member 137. In this illustrated example, the retaining member 137 may comprise a first clip 139*a* and a second clip 139*b* that are in a generally vertical alignment with one another. In such a retainer arrangement, when the feature collapses and the proximally located first wall 141*a* moves in a distal direction towards the second wall, the first clip 139*a* will engage the second clip 139*b* such that they can no longer move apart axially. Various other solutions exist such as interference fits, bi-stable components such that once collapsed beyond a certain point they remain in that state. In an alternative example, the collapsible feature may be a deformable feature that compresses under force but takes a certain amount of time to return to its pre-compressed shape (e.g., 1 hour, 1 day, 1 week, etc). For example, this could be achieved using a damping system such as an air containment and slow release valve.

Retaining the collapsible feature in its collapsed state may be beneficial for a variety of reasons. For example, once the medicated module 104 is removed from the drug delivery device 102, the user may have a visual means of differentiating between a used and an unused medicated module. The body of the medicated module may include a see-through window (not shown) showing the collapsible feature. Thus, a user may be able to visually detect whether the medicated module is used or not by visually detecting whether the collapsible feature is compressed or not. Further, if the collapsible feature is generally transparent, the user may be able to determine whether the collapsible feature contains any medicament Additionaly, retaining the collapsible feature in its collapsed state may also reduce the risk of "suck-back" at the end of a dispense stroke. That is, when the collapsible feature transitions from a relaxed state at the start of dose delivery then is compressed at the end of dose delivery, the collapsible feature will tend to return to its starting relaxed state as soon as the force acting upon it (i.e., the push rod 108) has been removed. If it starts to return to it's relaxed state after the removal of the biasing force, there is a chance that it will try to suck dispensed fluid back Still further, retaining members may be used to provide audible/tactile feedback to indicate completion of a dispense stroke. This may be beneficial so as to indicate to a user when the dispense process is complete and the needle may be safely removed from the injection site.

Figure 3:
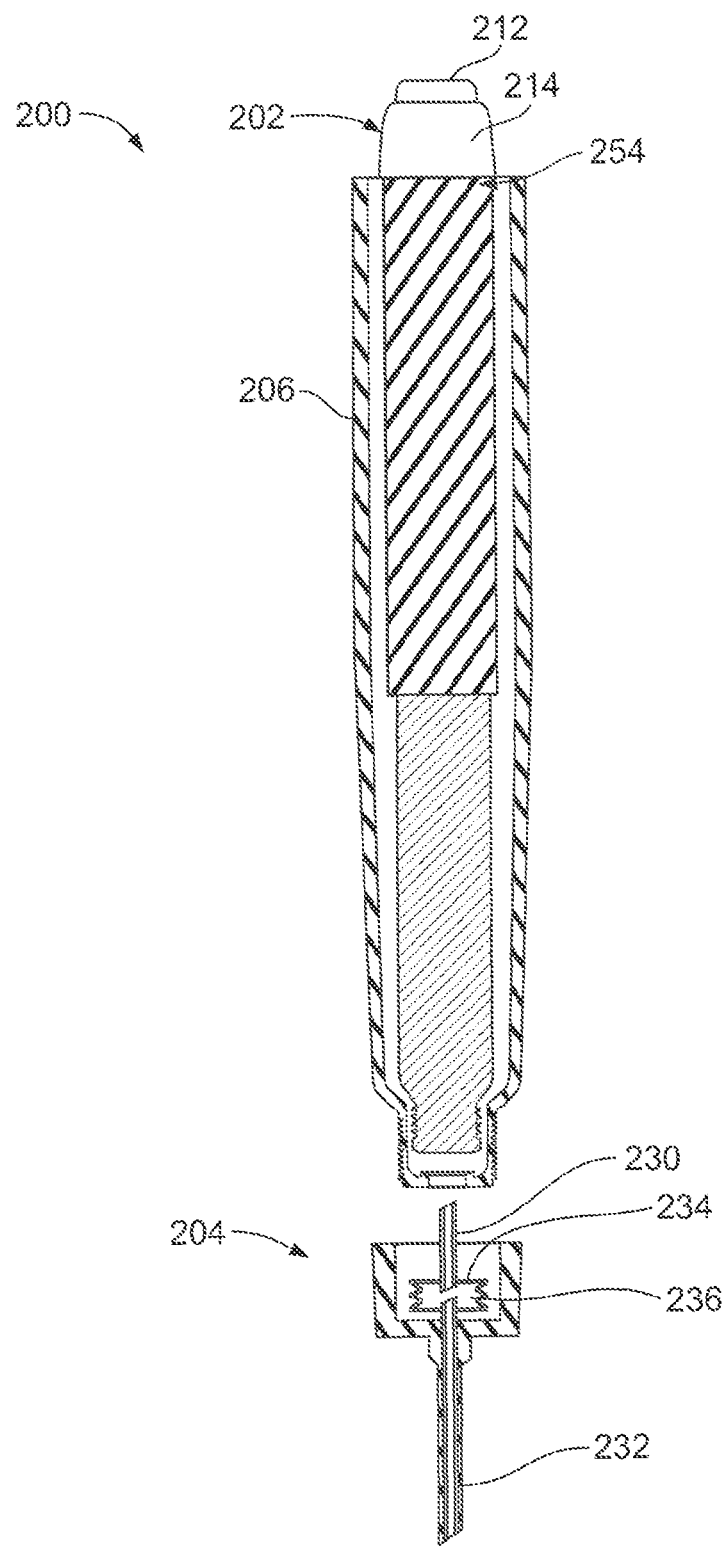
FIG. 3 illustrates a perspective view of an exemplary drug delivery system.
Figure 4:
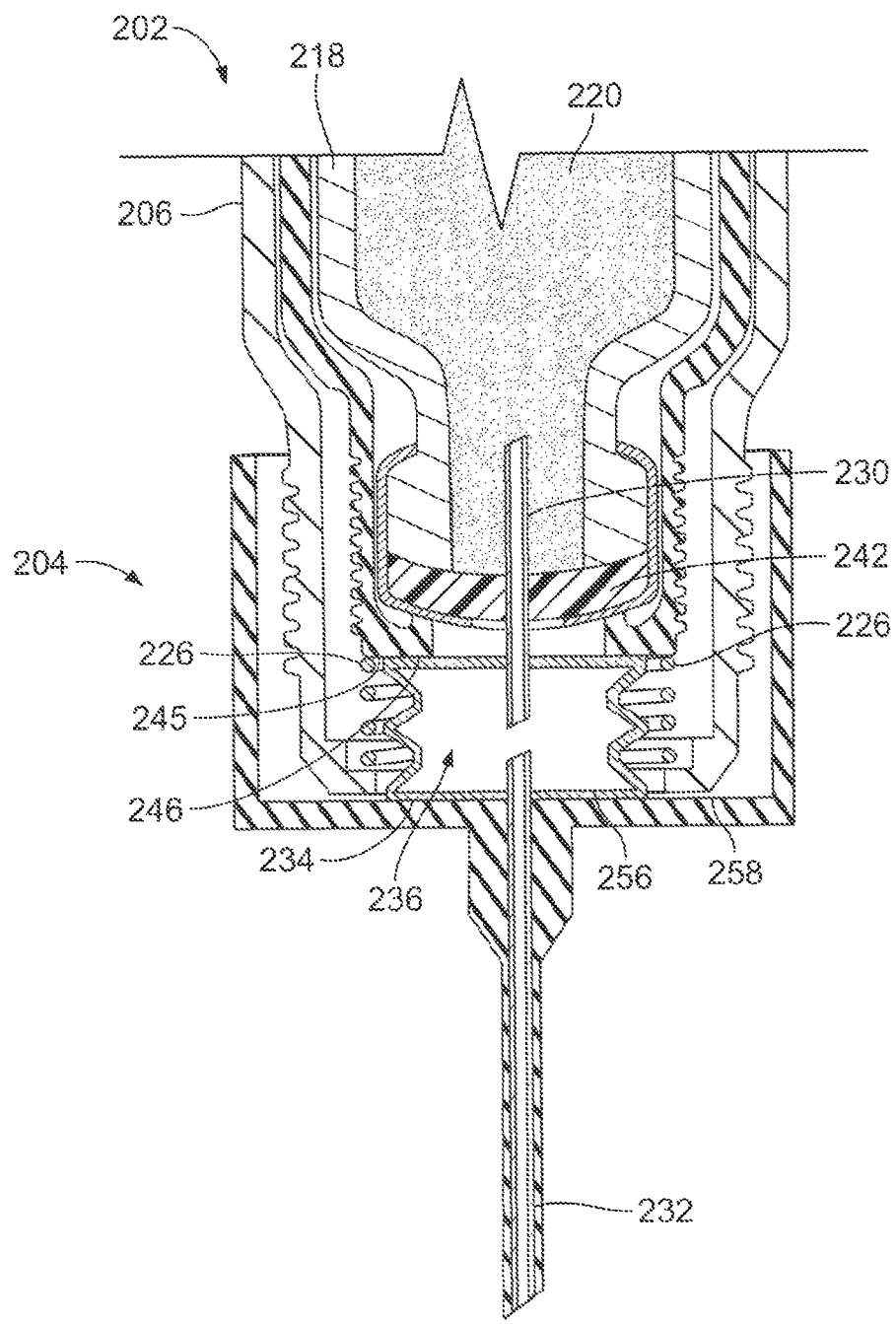
FIG. 4 illustrates a cross-sectional view of an exemplary medicated module attached to an exemplary drug delivery device.

An alternative embodiment of Applicants' proposed concept is depicted in FIGS. 3-4. This drug delivery system 200 is similar in certain respects to drug delivery system 100, and thus is not described in as great of detail. It should be noted, however, that many of the possibilities and permutations discussed above with reference to system 100 may equally apply to system 200. Similar to system 100, system 200 is a drug delivery system that includes a collapsible feature holding a secondary medicament, wherein the collapsible feature is compressed upon dispense, thus beneficially limiting or minimizing ullage. Further, the dose setter of the drug delivery system 200 is mechanically linked to the collapsible feature. However, the arrangement of the system 200 and compression of the collapsible feature in this alternative embodiment of system 200 is somewhat different than the embodiment discussed with reference to FIGS. 1-2. These differences are shown in FIGS. 3-4 and described in more detail below.

Figure 5:
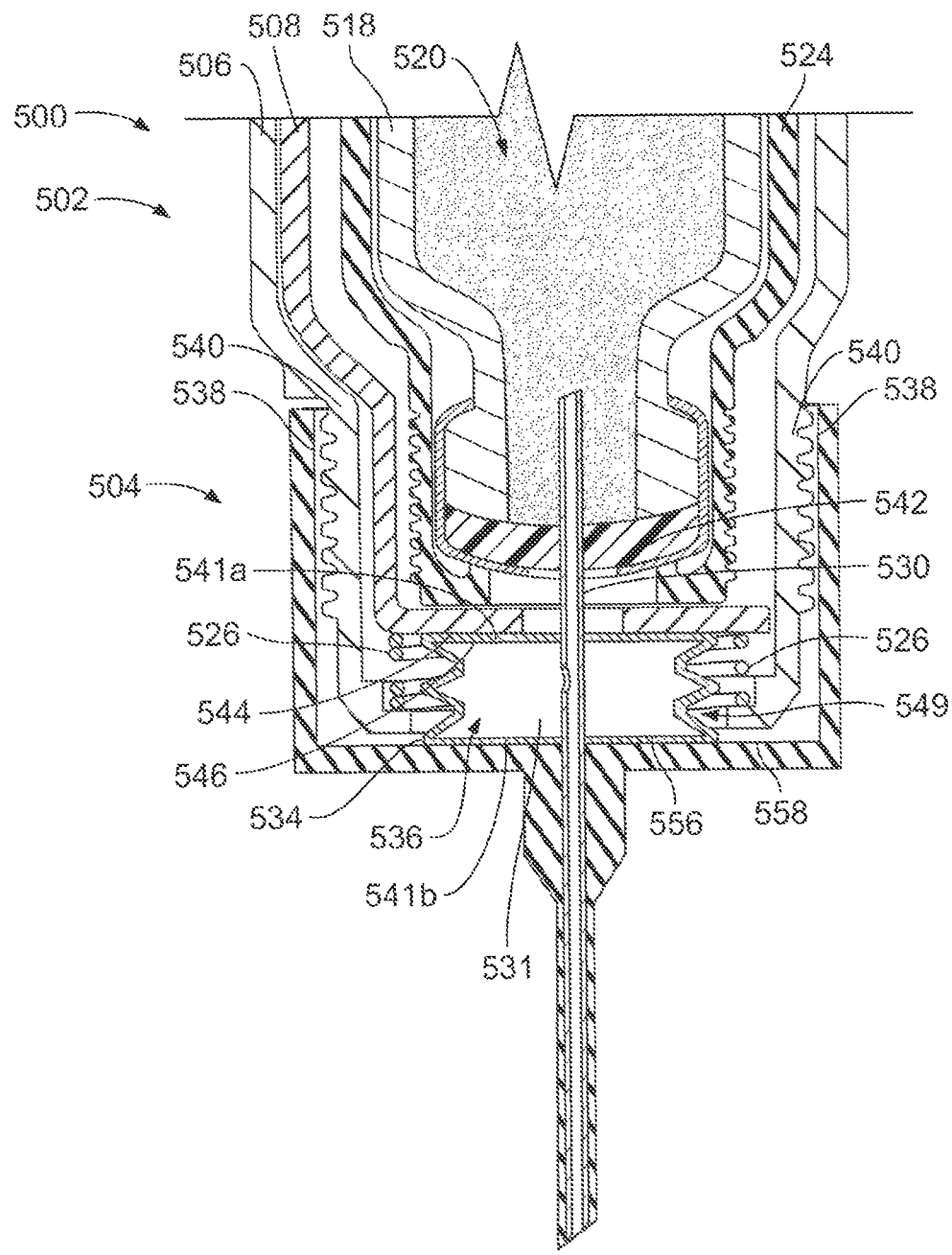
FIG. 5 illustrates a cross-sectional view of yet another exemplary medicated module attached to an exemplary drug delivery device.

In this alternative embodiment of Applicants' proposed concept, a drug delivery device 202 (which may be the same as or similar to standard drug delivery device 300 shown in FIG. 5) is contained within an outer shroud 206. The drug delivery device 202 is axially movable relative to the outer shroud 206 and is biased with a preloaded biasing feature, such as preloaded spring element 226, such that it protrudes from the outer shroud 206 prior to dispense, as illustrated in FIG. 3. The medicated module 204 attaches to the outer shroud 206 causing the engagement needle 230 located in the medicated module 204 to penetrate the septum 242 of the reservoir or cartridge 218 of the drug delivery device 202, as illustrated in FIG. 4. The needle 230 may be affixed to a top surface of a collapsible feature 234.

Once the engagement needle 230 has passed through the septum 242 of the cartridge 218, fluid connection is made between the first medicament 220 and a collapsible feature 234. In this example, the top surface 246 of the collapsible feature comes into contact with the lower surface 245 of the cartridge. The collapsible feature 234 is located in the medicated module 204 device and contains the fixed dose of second medicament 236.

After the module 204 is attached to the outer shroud 206, a user may set a user-settable dose of the first medicament 220. The dose of the drug delivery device 202 may be set in a usual manner (e.g., by dialing out an appropriate number of units of the primary medicament 220 with dose dial 214). Dispense of the first medicament 220 and the second medicament 236 may then be achieved via activation of the dosing mechanism of the drug delivery device 202.

Generally, during dispense, axial displacement of the dose button 212 forces the first medicament 220 to flow from the reservoir into the collapsible feature 234 via the first needle 230. Further, axial displacement of the dose button 212 forces medicament in the collapsible feature to flow out of the output needle 232. Still further, at a predetermined axial displacement of the dose button 212, the drug delivery device 202 overcomes a preloaded force of the biasing feature 226 and moves axially through the outer shroud 206. The axial movement of the drug delivery device 202 compresses the collapsible feature 234. The compression of the collapsible feature 234 forces at least some of a remaining amount of medicament in the collapsible feature 234 out of the second needle 236.

Specifically, during dispense, depression of the dose button 212 and dose dial 214 causes the variable dose of first medicament 220 to begin to flow from the cartridge into the collapsible feature 234 of the medicated module 204. Medicament is then dispensed through the output needle 232 (as the collapsible feature 234 is unable to expand). As discussed above, this medicament is likely a mixture of the first and second medicaments 220, 236. At the end of the variable dose of first medicament 220 dispense, the dose dial 214 contacts the end stop 254 located in the drug delivery device 202. Subsequent user-applied force to the dispense mechanism, sufficient to overcome the preloaded force of the spring element 226, causes the drug delivery device 202 to be displaced axially relative to the outer shroud 206.

As the drug delivery device 202 is displaced the lower face 245 of the cartridge compresses the collapsible feature 234. Similar to the example above, the lower face 256 of collapsible feature 234 may be restrained by the casework 258 of the medicated module 204. Compression of the collapsible feature 234 causes the remaining amount of medicament present within the collapsible feature to be dispensed through the output needle 232. Upon release of the dispense force by the user, the spring element 226 returns the drug delivery device 202 to its pre-dispensed axial position.

After the user finishes dispensing the medicament, the user may remove the output needle 232 from the injection site. Then, the depleted medicated module 204 may be disposed of. Assuming that the drug delivery device 202 still holds some first medicament 220, the drug delivery device 202 may be reused by the patient as required.

In an example of this alternative embodiment, the drug delivery system 200 may also be arranged such that the force required to (i) compress the spring element 226 and (ii) expel the medicament in the collapsible feature 234 through the outlet needle 232 is lower than the force to advance the dispensing mechanism 214 of the drug delivery device 202. In such an arrangement the fixed dose of second medicament 236 would be delivered first, because the collapsible feature 234 would be collapsed before the dispensing action forces the first medicament 220 to flow from the primary reservoir 218 to the output needle 232. This arrangement may be beneficial, as it may reduce the risk of a patient not receiving the full dose of both medicaments if they inadvertently stop the dispense stroke once the dose had been dispensed from the drug delivery device (i.e., before the collapsible feature 234 is compressed).

In yet another alternative embodiment in accordance with Applicants' proposed concept, a drug delivery system may comprise a standard needle assembly, with a side core hole near its root. This drug delivery system is similar in many respects to drug delivery systems 100 and 200, and thus is not described in as great of detail. It should be explicitly noted, however, that many of the possibilities and permutations discussed above with reference to system 100 and 200 may equally apply to this system. Similar to system 100 and system 200, this alternative embodiment comprises a drug delivery system that includes a collapsible feature holding a secondary medicament, wherein the collapsible feature is compressed upon dispense, thus beneficially limiting or minimizing ullage. Further, the dose setter is mechanically linked to the collapsible feature. However, the arrangement of this system and compression of the collapsible feature is somewhat different. These differences are shown in FIG. 5 and described in more detail below.

FIG. 5 illustrates yet another alternative embodiment of a medicated module having certain similar features than the medicated modules illustrated in FIGS. 2 and 4 with similar features designated by similar reference numbers. As illustrated in FIG. 5, the medicated module 504 may be attached to the drug delivery device 502. Unlike the medicated modules illustrated in FIGS. 2 and 4, however, the medicated module 504 includes a single double ended needle 530. This medicated module further comprises a collapsible feature 534 holding a second medicament 536. In an example, the second medicament 536 located in the collapsible feature 534 comprises GLP-1 and the first medicament 520 located in the primary drug delivery device 502 comprises insulin. However, other examples of medicaments and combinations of medicaments are possible as well. In this example, the double-ended needle 530 comprises at least one side hole 531 that allows the needle to be in fluid communication with the collapsible feature 534. Preferably, in one arrangement, a proximal end of the double-ended needle 530 would be provided with a one way valve to prevent fluid from the collapsed section from flowing into the cartridge of the drug delivery device.

When a dose is to be administered, the push rod will push against the container and then collapses the container. As the collapsible feature 534 collapses in one direction (axially), this action will force the second medicament 536 out of the distal end of the double-ended needle 530. The top and bottom surfaces 541 a-b may be rigid such that the needle 530 could be fixed in them. Full collapse of the flexible member 534 will therefore block the side hole 531 of the needle 530. With this hole 530 blocked, no further second medicament 536 can flow. Therefore, in this situation, only the primary medicament 520 can then be administered during the remainder of the dose administration.

This medicated modules disclosed herein may be attached to a drug delivery device, such as the drug delivery device 300 shown in FIG. 6, prior to its insertion into an outer sleeve. In this alternative embodiment, the sleeve may have a replaceable end cap including a medicament-filled, collapsible feature already attached. Upon insertion, the standard needle may pierce the upper and lower surfaces of the collapsible feature such that the side core hole was in fluid communication with the medicament contained therein.

Dispense would occur broadly as described for the alternative embodiment described above with reference to FIGS. 3-4, except that in this instance it would be preferable for the system to be arranged such that the axial force to compress the collapsible feature was less than the force to dispense from the multi-use device. In this way, a final compression of the collapsible feature during dispense of the fixed dose medicament would act to block off the side core hole in the needle. This would then force direct fluid flow from the multi-use device through the needle as dispensing from this device occurs.

Applicants' proposed concept also includes a method for dispensing a user settable dose of a first medicament and a non-user-settable dose of a second medicament using a single dispense interface. The method includes the step of attaching a medicated module to a drug delivery device. The drug delivery device comprises a single dose setter operably connected to a primary reservoir containing the first medicament. Further, the medicated module comprises (i) a collapsible feature holding the second medicament and (ii) the single dispense interface having an output needle. The drug delivery device and medicated module are each configured such that the single dose setter is mechanically linked to the collapsible feature after attachment of the medicated module to the drug delivery device.

The method further includes the step of setting a dose of the first medicament contained in the primary drug reservoir using the single dose setter of the drug delivery device. Still further, the method includes the step of activating a dose button of the single dose setter to cause a dose of the first medicament from the primary drug reservoir to flow into and/or through the collapsible feature. And yet still further, the method includes the steps of forcing a first and second medicament in the collapsible feature to flow out the output needle and forcing the mechanically-linked dose setter to compress the collapsible feature, thereby forcing at least some of a remaining amount of medicament in the collapsible feature out the output needle.

Numerous examples of drug delivery systems in accordance with Applicants' proposed concept have been described above. As mentioned above, the drug delivery systems in accordance with Applicants' proposed concept beneficially limit or minimize ullage of the drug delivery system. Because the collapsible features of the medicated modules in accordance with Applicants' proposed concepts have a smaller post-dispense volumes than pre-dispense volumes, the ullage that may be present in the medicated modules after dispense is reduced.

Beneficially, limiting the ullage in the medicated module may help reduce the amount of medicament that is wasted by being left in the medicated module after use. Further, limiting the ullage in the medicated module may help reduce the degree to which the dialed dose (i.e., what is indicated to the patient on the dose setter) on the primary delivery device needs to be offset to accommodate for the effect of ullage in the single-use medicated module.

An additional benefit of given embodiments of Applicants' proposed concept (e.g., when a standard drug delivery device is connected to an outer housing) is that the larger diameter required for the medicated module to be attached to the drug delivery device means that standard injection needles could not inadvertently or deliberately used with the drug delivery device and vice versa (i.e., the medicated modules including the collapsible features). This beneficially serves to ensure that only a correct medicated module is used with a given drug delivery device.

In the example drug delivery systems described herein, the dispense mechanisms of the drug delivery systems are axially-driven dispense mechanisms. However, it should be understood that drug delivery systems in accordance with Applicants' proposed concepts having other types of dispense mechanism are also possible.

The connection or attachment between the medicated module of the above described embodiments may contain additional features (not shown), such as connectors, stops, splines, ribs, grooves, and the like design features, that ensure that specific medicated modules are attachable only to matching drug delivery devices. Such additional features would prevent the insertion of a non-appropriate medicated module to a non-matching injection device.

The shape of the medicated module may be a cylindrical body or any other geometric shape suitable for defining a fluid reservoir or for containing discrete self-contained reservoir of the medicament in the medicated module and for attaching one or more needle cannula. The medicated module can be manufactured from glass or other drug contact suitable material. The integrated output needle can be any needle cannula suitable for subcutaneous or intramuscular injection. Preferably the medicated module is provided by a drug manufacturer as a stand-alone and separate device that is sealed to preserve sterility. The sterile seal of the module is preferably designed to be opened automatically, e.g. by cutting, tearing or peeling, when the medicated module is advanced or attached to the drug delivery device by the user.

Applicants' medicated module may be designed to operate in conjunction with a multiple use injection device, preferably a pen-type multi-dose injection device. The injection device could be a reusable or disposable device. By disposable device it is meant an injection device that is obtained from the manufacturer preloaded with medicament and cannot be reloaded with new medicament after the initial medicament is exhausted. The device may be a fixed dose or a settable dose and preferably a multi-dose device, however, in some cases it may be beneficial to use a single dose, disposable device.

A typical drug delivery device contains a cartridge or other reservoir of medication. This cartridge is typically cylindrical in shape and is usually manufactured in glass. The cartridge is sealed at one end with a rubber bung and at the other end by a rubber septum. The drug delivery pen is designed to deliver multiple injections. The delivery mechanism is typically powered by a manual action of the user, however, the injection mechanism may also be powered by other means such as a spring, compressed gas or electrical energy.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A medicated module attachable to a drug delivery device the drug delivery device comprising a housing, a reservoir for a liquid and a dose button, the medicated module comprising:
   an outer body having a hub;
   a push rod axially slidable with respect to the outer body;
   a proximal first needle configured to establish fluid communication with the liquid in the drug delivery device's reservoir after the medicated module is attached to the drug delivery device;
   a distal second needle configured for attachment to the hub for dispensing liquid;
   a collapsible container holding a medicament, wherein the container is arranged between the outer body and push rod and in fluid communication with the first needle and the second needle;
   wherein, during dispense the push rod moves axially relative to the outer body and the housing of the drug delivery device and compresses the container to force, at least some of a remaining amount of medicament in the container out of the second needle.

2. A medicated module according to claim 1 comprising a biasing feature positioned between the push rod and the outer housing which is configured to prevent compression of the container until a predetermined displacement of the dose button, wherein said biasing feature is preloaded with a force, and
   wherein, during dispense, the preload of the biasing feature is overcome at a predetermined displacement of the dose button to allow compression of the container.

3. A drug delivery system to deliver a user-settable dose of a first medicament and a non-user settable dose of a second medicament through a single dose setter and a single dispense interface, the drug delivery system comprising:
   a drug delivery device comprising:
   an outer housing disposed around a single dose setter operably connected to a primary reservoir of medicament including the first medicament;
   a dose button operably connected to the primary reservoir of medicament;
   a push rod axially moveable with respect to the outer housing; and
   a medicated module attachable to the drug delivery device comprising,
   a proximal first needle configured to establish fluid communication with the liquid in the drug delivery device's reservoir after the medicated module is attached to the drug delivery device;

a distal second needle configured for dispensing liquid;
a collapsible container holding a medicament, wherein the container is arranged between and in fluid communication with the first needle and the second needle;
wherein, the container is configured such that during dispense, the compression of the container is allowed so that compression of the container forces at least some of a remaining amount of medicament in the container out of the second needle;
wherein the drug delivery system comprises a biasing feature preloaded with a force arranged to bias the pushrod in the axial direction, wherein the biasing feature is part of either one of the medicated module and the drug delivery device and wherein the biasing feature is operably connected to the push rod when the medicated module is attached to the drug delivery device.

4. The drug delivery system of claim 3, wherein the push rod comprises a distal end and a proximal end, and wherein, at the predetermined axial displacement of the dose button, (i) the dose setter contacts the proximal end of the push rod and (ii) the distal end of the push rod contacts the container.

5. The drug delivery system of claim 3, wherein, after attachment, a distal end of the push rod is disposed between a distal end of the primary reservoir and a proximal end of the container.

6. The drug delivery system of claim 3, wherein, after attachment, a distal end of the push rod contacts a proximal end of the container.

7. The drug delivery system of claim 3, wherein the drug delivery system is configured to allow the push rod to return to a pre-dispense position after the push rod compresses the container.

8. The drug delivery system of claim 7, wherein the dose setter comprises a recess configured to allow the push rod to return to a pre-dispense position after the push rod compresses the container.

9. The drug delivery system of claim 8, wherein the biasing feature forces the push rod to return to a pre-dispense position.

10. The drug delivery system of claim 3, wherein the container abuts a lower distal internal surface of the medicated module.

11. The drug delivery system of claim 3, wherein during dispense at a predetermined displacement of the dose button, the dose button forces the push rod to move axially in the distal direction, wherein the axial movement of the push rod compresses the container, and wherein the compression of the container forces at least some of the remaining amount of the medicament in the container out of the second needle.

12. A drug delivery system to deliver a user-settable dose of a first medicament and a non-user settable dose of a second medicament through a single dose setter and a single dispense interface, the drug delivery system comprising:
(i) a drug delivery device comprising:
a housing including the single dose setter operably connected to a primary reservoir of medicament including the first medicament;
a dose button operably connected to the primary reservoir of medicament; and
(ii) an outer shroud, wherein the outer shroud holds the drug delivery device, and wherein the drug delivery device is axially moveable relative to the outer shroud and is biased with a preloaded biasing feature;
(iii) a medicated module attachable to the drug delivery device comprising,
a proximal first needle configured to establish fluid communication with the liquid in the drug delivery device's reservoir after the medicated module is attached to the drug delivery device;
a distal second needle configured for dispensing liquid;
a collapsible container holding a medicament, wherein the container is arranged between and in fluid communication with the first needle and the second needle;
wherein, the container is configured such that during dispense, the compression of the container is allowed so that compression of the container forces at least some of a remaining amount of medicament in the container out of the second needle;
wherein the drug delivery system comprises a biasing feature preloaded with a force arranged to bias the outer shroud in the axial direction, wherein the biasing feature is part of either one of the medicated module and the drug delivery device and wherein the biasing feature is operably connected to a distal internal surface of the outer shroud and a distal external surface of the drug delivery device when in attached condition.

13. The drug delivery system of claim 12, wherein, after dispense, the biasing feature forces the drug delivery device to a pre-dispense position.

14. The drug delivery system of claim 12, wherein a first force required to overcome the preloaded force of the biasing feature is lower than a second force required to axially displace the dose button during dispense.

15. The drug delivery system of claim 12, wherein during dispense, at a predetermined displacement of the dose button, the drug delivery device overcomes the preloaded force of the biasing feature and moves axially through the outer shroud, wherein the axial movement of the drug delivery device compresses the container, wherein the compression of the container forces at least some of the remaining amount in the container out of the second needle.

* * * * *